United States Patent [19]

Kollar et al.

[11] Patent Number: 4,774,842

[45] Date of Patent: Oct. 4, 1988

[54] HAND-HELD APPARATUS TO NONDESTRUCTIVELY TEST SUBSURFACE STRUCTURE

[75] Inventors: Raymond J. Kollar; Richard T. Melvin, both of St. Louis County, Mo.

[73] Assignee: McDonnell Douglas Corporation, Long Beach, Calif.

[21] Appl. No.: 830,947

[22] Filed: Feb. 19, 1986

[51] Int. Cl.$^4$ .......................................... G01N 29/04
[52] U.S. Cl. ...................................... 73/640; 73/641; 73/633; 73/621
[58] Field of Search ................. 73/639, 583, 621, 105, 73/640, 635, 641, 637, 638, 633

[56] References Cited

U.S. PATENT DOCUMENTS

| | | | |
|---|---|---|---|
| 3,289,468 | 12/1966 | Van Der Veer et al. | 73/641 |
| 3,628,375 | 12/1971 | Pagano | 73/639 |
| 3,824,843 | 7/1974 | Gebeshuber et al. | 73/640 |
| 4,304,133 | 12/1981 | Feamster, III | 73/633 |
| 4,462,255 | 7/1984 | Guess et al. | 73/633 |

Primary Examiner—Stewart J. Levy
Assistant Examiner—Louis M. Arana
Attorney, Agent, or Firm—James M. Skorich; George W. Finch; John P. Scholl

[57] ABSTRACT

A plurality of ultrasonic transducers mounted linearly on a belt that is contained and supported by a housing. The housing has wheels and handles mounted on its sides to allow an operator to grasp the apparatus and roll it across the surface of a test object along a line normal to the belt. The transducers are electrically connected to various devices which enable pulse echo testing to be performed on the test object and make the results immediately available as a picture either on paper or on a video monitor. The belt is moved laterally and cyclically back and forth as the apparatus is rolled longitudinally and the transducers are sequentially excited to emit ultrasonic waves, thus testing a swath having a width equal to the extremes of lateral motion of the line of transducers. A dynamic counterbalance swings 180° out of phase with the cyclic motion of the belt, and serves to damp out the vibration generated by the belt's motion. The transducers are held abutting the surface of the test object and oriented so that the emitted ultrasonic waves are always normally incident to this surface, regardless of whether the surface is curved or flat.

26 Claims, 7 Drawing Sheets

HAND-HELD APPARATUS TO NONDESTRUCTIVELY TEST SUBSURFACE STRUCTURE

BACKGROUND OF THE INVENTION

1. Field of the Invention

This invention relates to the nondestructive testing of the subsurface structure of an object and, more particularly, to employing a sensing probe capable of continuously moving and operating over curved surfaces.

2. Descripton of the Prior Art

An ever-increasing number of aircraft parts are being constructed from laminated layers of high strength material because parts fabricated in this manner are lighter and easier to manufacture (especially where the part includes compound curves) than comparable metal parts. However, such laminate composite parts are susceptible to bonding flaws which cannot be detected by visual inspection. In addition, the resin used in the lamination process is vulnerable to degradation from exposure to ultraviolet rays, deleteriously affecting the structural integrity of the part and remaining virtually undetectable until resulting in a fracture. The impact of a heavy object on a laminate composite part can also cause internal cracks while leaving the surface undamaged.

The need to provide for the nondestructive subsurface inspection of laminate composite parts, both immediately after their manufacture as well as periodically in the field, has given rise to two systems which inspect the subsurface material using ultrasonic waves: through transmission and pulse echo.

Through transmission apparatus uses an emitting transducer to direct ultrasonic waves at a normal angle of incidence to the opposing surface of the part to be tested. A receiving transducer is located on the opposite side of the part and is aligned with the sending transducer. The part is inspected for flaws by measuring the attenuation suffered by the ultrasonic waves in passing through the part, and comparing the actual attenuation with the value that would be obtained in the absence of any irregularities.

There are several inherent constraints that limit the utility of testing with through transmission apparatus. The receiving transducer must be located on the side of the thickness of material being tested that lies opposite the side that faces the emitting transducer, and the receiving transducer must remain aligned with the emitting transducer. This requires access to the back side of the composite thickness being tested, and precludes using through transmission apparatus to test assembled parts which enclose a volume, for example, a wing which encloses a fuel tank. If such parts are to be tested using through transmission, the individual sides comprising the part must be tested before final assembly. Periodic field testing of such parts after their assembly is not possible.

In addition, reflection from the opposing surface attenuates the strength of the incident wave that continues through the test object, with the amount of attenuation increasing with an increase in the difference between the angle of incidence and normality. Thus, although it is not required that the incident ultrasonic wave be precisely normal, it is desirable to obtain an angle of incidence as close to normal as possible in order to maximize the amplitude of the wave passing through the test object and remain safely above the noise level of the receiving transducer.

The requirements of keeping the receiving and emitting transducers aligned and maintaining an approximately normal angle of incidence for the impinging ultrasonic waves give rise to considerable design problems when the test object includes curved surfaces. The problem of testing over curved surfaces has typically been resolved by interrupting the testing to change the position of the part. A recent development intended to reduce the time consumed by the incessant interruptions required to reposition the test part is disclosed by U.S. patent application Ser. No. 760,265: "Surface Tracking Apparatus", invented by Gerald D. Garner and Walter E. Wozniak and filed on July 29, 1985.

The apparatus of Garner et al. keeps the part being tested stationary, and instead continually orients the emitting transducer to maintain normal incidence between the ultrasonic waves and the opposing surface of the part, as well as orienting the receiving transducer to keep it aligned with the emitting transducer. The device successfully performs its intended function but, as can be seen from the perspective drawing provided by FIG. 5, it is quite large and would be difficult to move. In addition, it is primarily suited to inspecting laminate composite parts prior to the final assembly of the aircraft.

The gantry used in Garner et al. to move the emitting and receiving transducers relative to the part is also an integral part of devices which approach the problem of testing curved surfaces by changing the position of the part relative to the inspection apparatus, and thus similarly compromises their portability and utility for testing parts on assembled vehicles.

The pulse echo system employs one transducer to both emit ultrasonic waves at an angle of incidence normal to the opposing surface of the part and subsequently receive the reflected echoes. A first echo is reflected from the opposing surface, while a second is reflected from either a subsurface anomaly or the back surface of the part. The time interval between the reception of the first and second echoes is compared with the theoretical time interval that would be required if the second echo was reflected by the back surface of the part, with an actual time interval less than the theoretical value being indicative of the second echo reflecting off of a subsurface anomaly.

The pulse echo system can be modified to enable it to ascertain the nature of any irregularity as well as its presence and subsurface depth by comparing the amplitude of the first and second echoes. However, through transmission remains the preferred system for obtaining information regarding the makeup of an anomaly because of its greater tolerance for deviation from normality of the impinging wave, which translates into fewer interruptions to change the position of a test part having a curved surface.

The apparatus disclosed in Garner et al. can also be used for pulse echo testing but, as previously alluded to, lacks the portability desired for field use and is primarily suited for the testing of laminate composite parts prior to the final assembly of the aircraft. Other pulse echo apparatus reposition the part in order to obtain normality between the emitted ultrasonic waves and the part's surface, but as they typically employ a gantry resembling that pictured in FIG. 5 of Garner et al. to move the transducer relative to the part, they are similarly not adapted for use in the field or for testing after final assembly of the aircraft.

However, as there is no need to position a receiving transducer on the opposite side of the part and keep it aligned with the emitting transducer, pulse echo apparatus is more suited to the requirements of field use than through transmission apparatus, and seeral attempts have been made to fashion a portable device for testing laminate composites using this approach. An example is provided by U.S. Pat. No. 4,470,122 issued on Sept. 4, 1984, to Dennis P. Sarr.

Sarr discloses a probe which emits a nondestructive test signal and subsequently receives its echoes. The probe is manually moved across the surface of the object being tested by the operator. A light source is affixed to the probe, and its position is monitored by two scanning light sensors which are spaced apart from each other. The device can only be used over relatively flat surfaces, and the assembly containing the two scanning light sensors must be moved when the rectangular area defined by the sweep of their scan has been covered with the probe.

The inability of the apparatus disclosed in Sarr to test a section having a curved surface is a limitation which, as previously noted, has been the focus of creative effort in the prior art. This problem is especially significant because the advantage in fabricating curved parts from laminated layers in comparison to using metal is certainly compromised when such parts cannot be easily and quickly tested in the field for subsurface flaws.

SUMMARY OF THE INVENTION

A plurality of ultrasonic transducers are mounted in a line on a flexible belt contained in a casing. The casing has handles to allow it to be easily grasped by an operator, and has wheels mounted on its sides to enable the operator to roll the apparatus across the surface of a part that is to be nondestructively tested. A spring mechanism holds the transducers in abutment against the opposing surface of the part with a constant, even pressure, and keeps them oriented so that the emitted ultrasonic waves are normally incident to the surface. The transducers are sequentially and periodically excited to the emit ultrasonic waves while the belt is moved laterally and harmonically back and forth and the casing rolled longitudinally across the part's surface at a right angle to the line of transducers.

Each transducer receives echoes from each emitted ultrasonic wave, and the time interval between the receipt of the first two echoes is indicative of the condition of the structure underlying the opposing surface. A dynamic counterbalance swings 180° out of phase with the cyclic motion of the belt, serving to damp out the vibration generated by the belt's motion that would otherwise interfere with the transducers reception of the echoes. As the casing is rolled across the surface, the apparatus completely inspects the subsurface structure underlying a swath having the width of the extremes of lateral motion of the line of transducers.

More particularly, each transducer in the array is electrically connected to equipment which obtains the time interval between the first and second echos generated by each emitted ultrasonic wave. An echo interval shorter than the interval which would ordinarily result from a first echo reflecting off of the opposing surface of the part and the second echo reflecting off of the part's back surface is indicative of a subsurface anomaly. The lateral position of each transducer is kept track of by a lateral position monitor, while the longitudinal position of the linear array of transducers is monitored by a longitudinal position monitor that is connected to one of the wheels mounted on the casing. The lateral and longitudinal position data are collected and collated in a position integrator, which continuously determines the two dimensional position coordinates for each transducer at each instant.

The position coordinates for each transducer and the echo intervals are fed into a microcomputer which collates them to form echo interval data points, with each data point being comprised of an echo interval and the position coordinates of the emitting transducer at the moment the echo interval was obtained. A plotter is connected to the microcomputer in order to graphically display the data points on paper. Also connected to the microcomputer is a video monitor which can graphically display the data points on its video screen concurrently with the testing of a cross section of the part.

The present invention is a light, portable hand-held device, and thus eminently suited for use in the field. This utility is enhanced by the capability of the apparatus to present a picture of the subsurface structure of the part being inspected on a video screen concurrently with its inspection.

The mounting of the array of transducers in a line on a flexible belt, combined with the mounting of the belt in a casing which rolls across the surface of the test part at a right angle to the line of transducers, allows testing over a surface which curves along the line of transducers as well as along a line normal to the line of transducers, and thus provides for testing over a surface having a compound curvature. The invention can inspect an unbroken swath having a width equal to the extremes of lateral motion of the line of transducers as the casing is rolled across the surface of the part being tested. The device is thus able to test a curved or uneven surface without requiring time consuming interruptions to change the position of either the test apparatus or the part being tested.

Since the belt supporting the line of transducers flexes to allow the transducers to remain in continuous contact with the surface of the test part as the transducers are being moved across its surface, the present invention displays a flat pattern of the test surface. The flat pattern maximizes surface resolution regardless of the contour of the test surface and eliminates distortion that would otherwise occur if the graphic representation of the test surface was obtained from a planar projection.

DETAILED DESCRIPTION OF THE DRAWINGS

Figure 1:
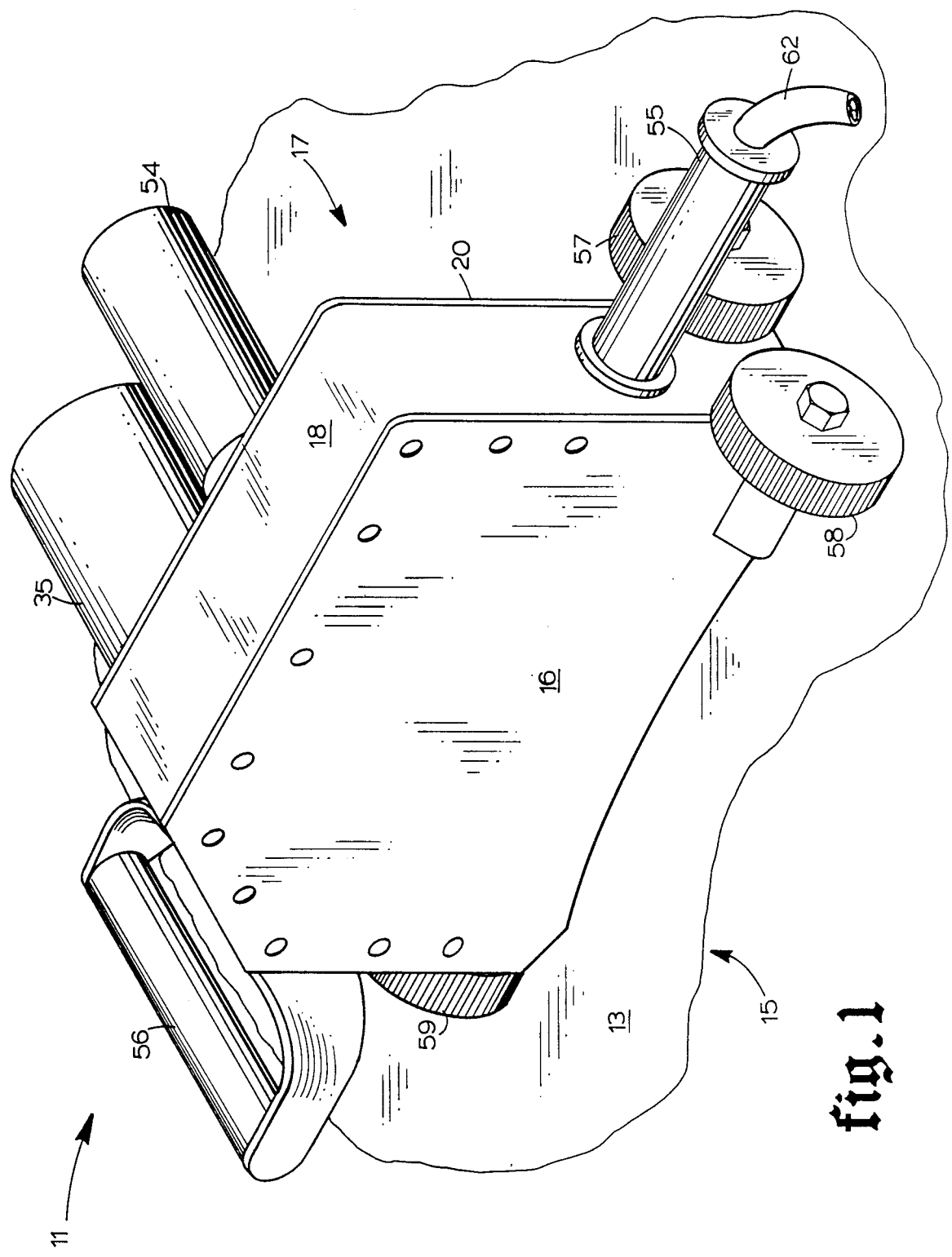
FIG. 1 is an isometric drawing of the preferred embodiment of the present invention operatively positioned on the surface of a test part.

Reference is now made to the drawings, and particularly to FIG. 1, which shows preferred embodiment 11 of the present invention operatively positioned on surface 13 of test part 15. Test part 15 is an aircraft part fabricated from a laminate composite. However, it should be noted that the present invention is not limited to such applications, but may be used to nondestructively test the subsurface condition of a wide variety of materials and objects.

Figure 2:
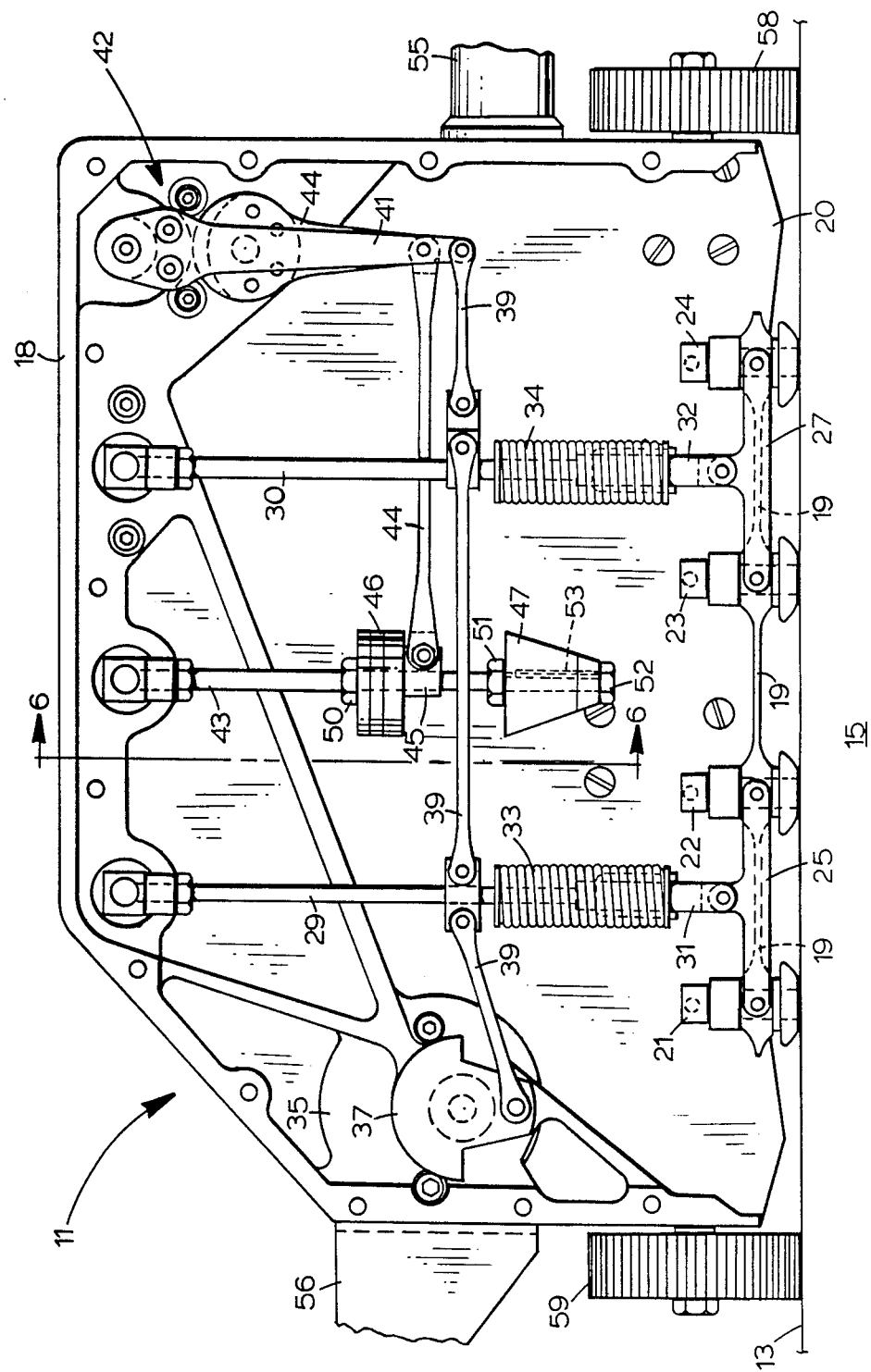
FIG. 2 is the front view of the preferred embodiment with the front cover plate removed in order to show its moving mechanical parts.
Figure 3:
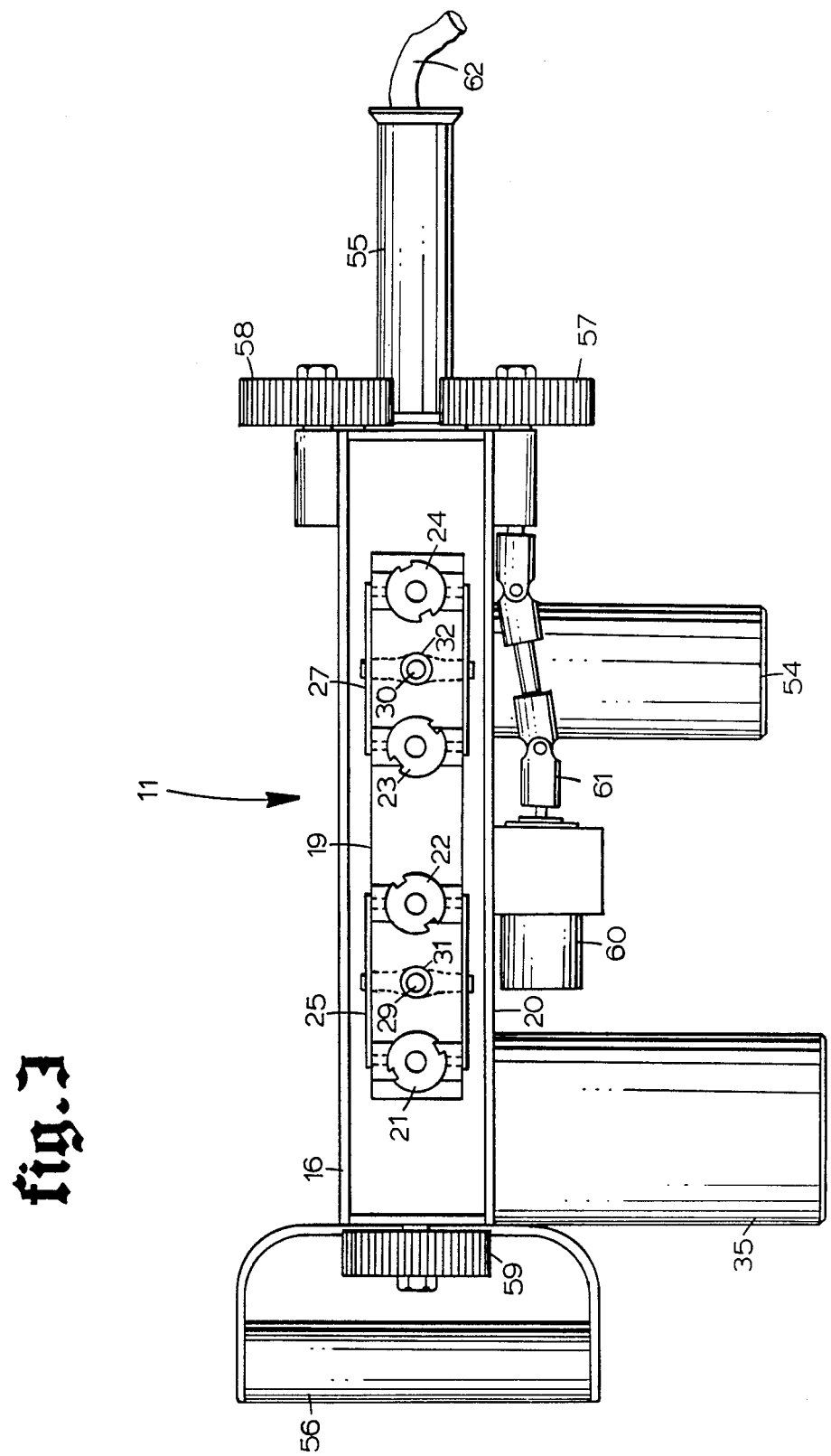
FIG. 3 is the bottom view of the preferred embodiment.

Casing 17 is a housing and integrative support for preferred embodiment 11. Casing 17 is comprised of front cover plate 16, frame 18, and back cover plate 20. FIGS. 2 and 3 show the front and bottom views, respectively, of preferred embodiment 11. Cover plate 16 is removed in FIG. 2 in order to show the moving parts of preferred embodiment 11. Flexible belt 19 holds a linear array of four ultrasonic transducers, transducers 21, 22, 23, and 24. This belted array is supported by articulated linkages 25 and 27, with transducers 21 and 22 being rotatably connected to linkage 25, and transducers 23 and 24 being rotatably connected to linkage 27.

Pivoting arms 29 and 30 are rotatably suspended from the top of frame 18 and are constrained to rotate about respective axes that lie parallel to the intended direction of travel of casing 17, for reasons that will be subsequently become clear. Arm extensions 31 and 32 extend from the bottoms of pivoting arms 29 and 30, respectively, and are slideably attached thereto to provide for relative axial movement. The ends of arm extensions 31 and 32 that are not slideably attached to pivoting arms 29 and 30 are rotatably attached to articulated linkages 25 and 27, respectively. This configuration allows linkages 25 and 27 to rotate about respective axes that are parallel to the axes of rotation of pivoting arms 29 and 30.

Coil spring 33 is annularly situated about pivoting arm 29 and arm extension 31, with the upper part of the spring being attached to pivoting arm 29 and the lower end of the spring being attached to arm extension 31. The respective points of attachment are positioned such that coil spring 33 is in compression, thereby forcing arm extension 31 and articulated linkage 25 downwards towards surface 13, and thus keeping transducers 21 and 22 in contact with surface 13. The relative positions and operative relationships between coil spring 34, pivoting arm 30, arm extension 32, articulated linkage 27, and transducers 23 and 24 are the same as heretofore discussed in detail with respect to coil spring 33, pivoting arm 29, arm extension 31, articulated linkage 25, and transducers 21 and 22.

Rotary motor 35 is a variable speed electric motor which passes through back cover plate 20 and is attached to frame 18. Crank shaft 37 extends from rotary motor 35, and is rotatably connected to driving linkages 39. Driving linkages 39 rotatably interconnect with pivoting arms 29 and 30, such that the actuation of rotary motor 35 causes the harmonic pendulum motion of pivoting arms 29 and 30 about their points of rotational attachment to frame 18. This pendulum motion is translated into the harmonic lateral motion of transducers 21, 22, 23, and 24 across surface 13 through the system of interconnecting pivoting linkages hereinbefore described.

The high frequency harmonic lateral motion of transducers 21, 22, 23 and 24 and their connected linkages and pivoting arms could cause vibration of a magnitude sufficient to be detected by transducers 21, 22, 23 and 24, and could thus induce a spurious output signal that would interfere with the transducer output signals generated by the reception of ultrasonic echoes. In addition, such vibration could cause random lateral movement of casing 17 that would not be registered by the position sensors of preferred embodiment 11 (hereinafter discussed in detail) and thus, if not damped, would cause a cumulative error in the location of transducers 21, 22, 23 and 24. To avoid these problems, preferred embodiment 11 employs a dynamic counterbalance that harmonically swings 180° out of phase with the harmonic lateral motion of transducers 21, 22, 23 and 24, to damp out the vibration generated by this motion.

More particularly, driving linkages 39 are also rotatably connected to transmission linkage 41, which is in turn connected to phase reversing transmission 42. Dynamic counterbalance arm 43 is rotatably connected to the top of frame 18. Transmission output linkage 44 is an articulated linkage which rotatably connects phase reversing transmission 42 with dynamic counterbalance arm 43. More specifically, transmission output linkage 44 is rotatably connected at one end to phase reversing transmission 42, and is rotatably connected at its other end to sleeve 45. Sleeve 45 is threadably attached to dynamic counterbalance arm 43. The axial position of sleeve 45 on dynamic counterbalance arm 43 can be varied by disengaging it from transmission output linkage 44 and then rotating it about dynamic counterbalance arm 43.

Figure 6:
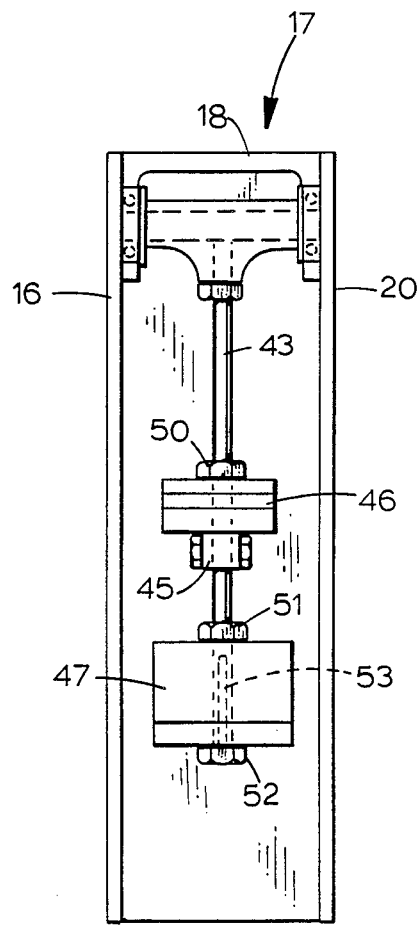
FIG. 6 is a sectional view of the preferred embodiment taken along line 6—6 in FIG. 2.

As illustrated in the sectional view provided by FIG. 6, as well as by FIG. 2, cylinder 46 and polyhedron 47 are each weights comprised of a plurality of removable plates, with each plate being manufactured from a high density material. It has been found that an alloy having a density of seventeen grams per cubic centimeter provides the requisite weight, yet allows cylinder 46 and polyhedron 47 to be shaped with a volume small enough to allow then to fit within the limited space available. Both weights are attached to dynamic counterbalance arm 43, with cylinder 46 being attached above transmission output linkage 44 and polyhedron 47 being attached below driving linkages 39 as well as transmission output linkage 44.

The axial position of cylinder 46 on dynamic counterbalance arm 43 is secured from above by locknut 50, and from below by abutment with sleeve 45. The axial position of polyhedron 47 on dynamic counterbalance arm 43 is secured from above by locknut 51 and from below by locknut 52. The axial positions of cylinder 46 and polyhedron 47 can be independently varied by rotating threaded locknut 50 and sleeve 45, and by rotating locknuts 51 and 52, respectively. However, the variation in the axial location of cylinder 46 is limited by the design constraint that the horizontal section of transmission output linkage 44 remain close to horizontal. Polyhedron 47 is restrained from rotating relative to dynamic counterbalance arm 43 by pin 53. The respective weights of cylinder 46 and polyhedron 47 may be varied by adding or shedding plates.

Phase reversing transmission 42 causes dynamic counterbalance arm 43 to move with a harmonic pendulum motion that is 180° out of phase with the pendulum motion of pivoting arms 29 and 30. The precise weights and axial locations of cylinder 46 and polyhedron 47 necessary to damp out the vibrations generated by the movement of the interconnected system of pivoting arms and linkages which cause the translational motion of transducers 21, 22, 23 and 24 can be calculated by one skilled in the art prior to the manufacture and assembly of preferred embodiment 11. However, the capability to independently adjust both the weights and locations of cylinder 46 and polyhedron 47 is desirable because the mass of each moving part and the parts' dynamic interaction may vary from their design parameters due to inaccuracies in manufacturing and assembly. In this event, the respective weights and axial locations of the two weights necessary to achieve damping should be empirically determined through iterative adjustments.

Pivoting arm 30 is connected to lateral position monitor 54. Lateral position monitor 54 passes through back cover plate 20 and is attached to frame 18. Lateral position monitor 54 uses the instantaneous angular position of pivoting arm 30 in addition to the static geometric relationships between transducers 21, 22, 23 and 24, and pivoting arms 29 and 30, to continuously calculate the lateral position of transducers 21, 22, 23 and 24.

Handles 55 and 56 are rigidly attached to frame 18 of casing 17 so that preferred embodiment 11 can be easily grasped and manipulated by an operator. Wheels 57, 58, and 59 are rotatably attached to casing 17 to allow preferred embodiment 11 to be rolled longitudinally across surface 13. The three wheels have a uniform radius designed to support casing 17 at a specific distance above surface 13 to ensure that transducers 21, 22, 23, and 24 all contact surface 13 with the same uniform downward pressure. A coupling gel must be applied to surface 13 to facilitate the conduction of the ultrasonic waves from ultrasonic transducers 21, 22, 23 and 24 into part 15, as well as the conduction of ultrasonic echoes from part 15 to the transducers. It has been found that the application of a film of water to surface 13 just before testing with preferred embodiment 11 provides satifactory acoustic conduction. However, any liquid that will provide the requisite acoustically conductive film on surface 13 can be used, and it is within the scope of the invention to apply such a film by means contained within or attached externally to casing 17, as well as by means separate from casing 17.

Wheels 57, 58 and 59 are attached to casing 17 along parallel axes. The configuration of wheels 57, 58 and 59, together with the support provided by belt 19 and the connected linkages and arm extensions, keeps the respective centerlines of transducers 21, 22, 23, and 24 oriented normally with respect to surface 13 even where the surface undulates. As particularly shown in FIG. 3, wheel 57 is connected to longitudinal position monitor 60 by means of monitor linkage 61 in order to allow longitudinal position monitor 60 to continuously monitor the longitudinal movement of preferred embodiment 11 across surface 13 of test part 15. Electrical cord 62 electrically connects preferred embodiment 11 to a power source (not shown) which provides the power necessary to operate transducers 21, 22, 23, and 24; rotary motor 35; lateral position monitor 54; and longitudinal position monitor 60.

Figure 4A:
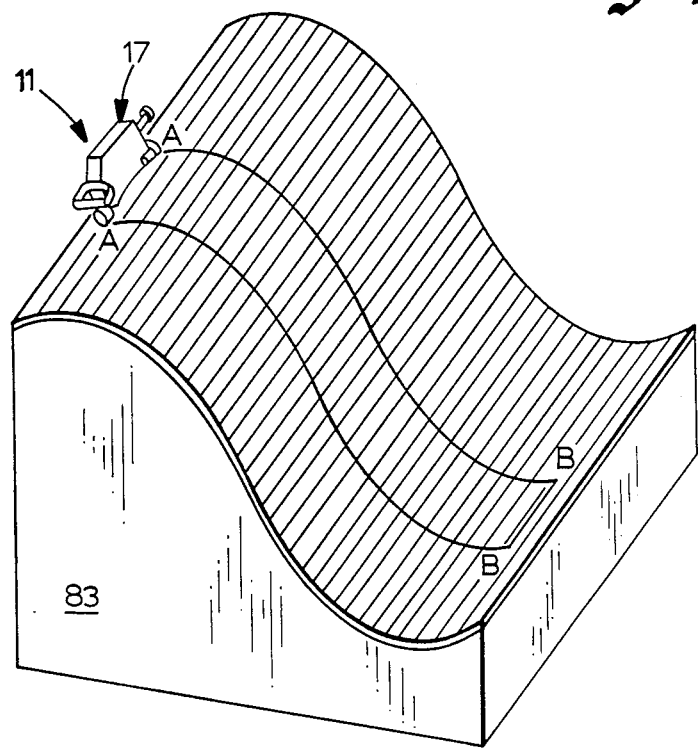
FIG. 4A is an isometric view of the preferred embodiment of the present invention located on the surface of a test part and prepared to test over a surface strip which curves along the intended line of travel of the preferred embodiment.
Figure 4B:
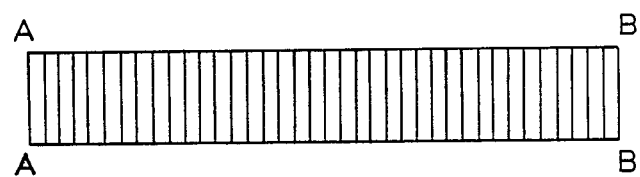
FIG. 4B shows the flat pattern displayed by the preferred embodiment upon testing the curved surface strip shown in FIG. 4A.

The ability of the present invention to keep the transducers normally aligned and in continuous contact with the underlying surface enables the present invention to display a flat pattern of the surface even where the surface undulates. To illustrate this feature, FIG. 4A shows preferred embodiment 11 poised to inspect surface strip AB on test part 83. Strip AB undulates along the direction of travel of casing 17. As shown in accompanying FIG. 4B, preferred embodiment 11 displays a flat pattern of strip AB that is free of any distortion caused by the undulations along the line of travel of casing 17.

Figure 5A:
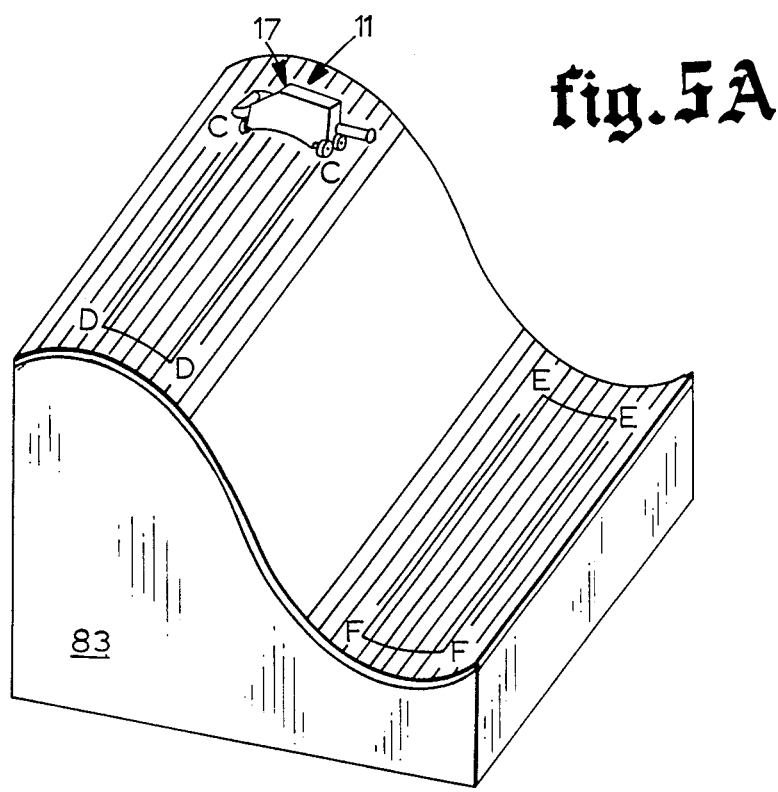
FIG. 5A is an isometric view of the preferred embodiment of the present invention located on the surface of the test part previously shown in FIG. 4A, and prepared to test over a convex strip and a concave strip. Both strips curve along a line normal to the direction of travel of the preferred embodiment.
Figure 5B:
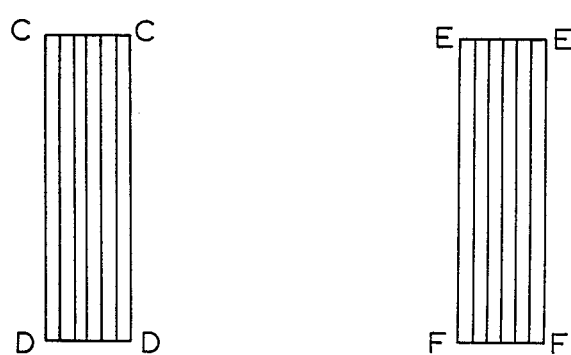
FIG. 5B shows the flat patterns displayed by the preferred embodiment upon testing the two curved surface strips shown in FIG. 5A.

The ability of belt 19 to flex allows preferred embodiment 11 to display a flat pattern of a surface which undulates along a line normal to the direction of travel of casing 17. FIG. 5A illustrates two examples of this ability on test part 83, one over convex strip CD and the other over concave strip EF. As shown in accompanying FIG. 5B, preferred embodiment 11 displays a flat pattern for both strips CD and EF.

The flat pattern provided by the present invention avoids distortion tat would otherwise result if the transducers were not kept in contact with the surface because a design situating the sensing transducers above the surface of the test part would require a planar projection of the surface, and a planar projection would necessarily distort undulations in the surface. In addition, the flat pattern enhances resolution of subsurface anomalies because it maximizes the lateral space between them. The aforementioned features which display a flat pattern for a surface which curves along the line of travel of casing 17 as well as for a surface which curves normal to the line of travel, also serve to present a flat pattern for a surface having a compound curvature.

Figure 7:
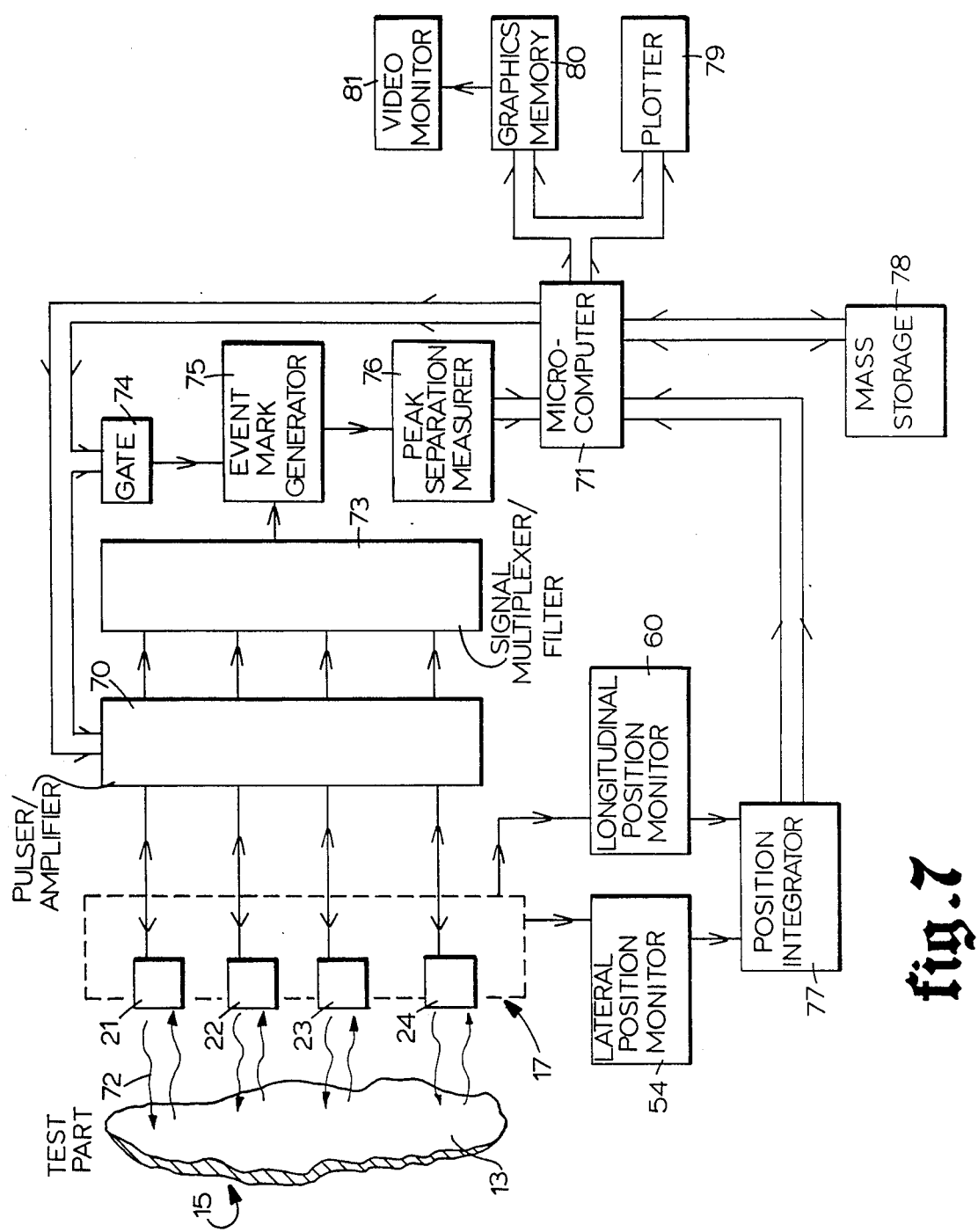
FIG. 7 is a schematic drawing of the preferred embodiment which graphically indicates how the test information is generated, processed and displayed.

FIG. 7 is a schematic drawing of preferred embodiment 11 of the present invention. Ultrasonic transducers 21, 22, 23 and 24 are located in casing 17, and are electrically connected to pulsar/amplifier 70. Pulsar/amplifier 70 sequentially excites transducers 21, 22, 23 and 24 with periodic voltage pulses upon receiving periodic trigger signals from microcomputer 71. Upon being excited, each transducer emits an ultrasonic wave 72 in the direction of part 15. Each ultrasonic wave 72 generates a first echo from surface 13 and a second echo at a later time from either the back surface of part 15 or a subsurface anomaly. The echos are received by the transducers, whereupon the acoustical energy is transformed into electrical energy in the form of voltage pulses. The respective voltage pulses from transducers 21, 22, 23 and 24 are input into pulsar/amplifier 70. The four channel output of pulsar/amplifier 70 is fed into signal multiplexer/filter 73, which filters the signals and combines them into one signal.

The trigger signals emanating from microcomputer 71 are also routed through gate 74. Gate 74 is electrically connected to event mark generator 75, and functions to control the signal being supplied event mark generator 75 by signal multiplexer/filter 73. More specifically, the opening of gate 74 is briefly delayed after its receipt of a trigger signal from microcomputer 71. The length of the delay is designed so that gate 74 opens immediately prior to the arrival at event mark generator 75 of the modulated pulse generated by the first echo from the ultrasonic wave 72 emitted as the result of the receipt by pulsar/amplifier 70 of the same trigger signal which concomitantly caused the opening of gate 74. Gate 74 subsequently remains open until it receives the next trigger signal in order to ensure that it will be open upon the arrival at event mark generator 75 of the modulated pulse generated by the second echo.

During each open interval of gate 74, event mark generator 75 generates a digital event along a time scale for each of the first and second echos from each ultrasonic wave 72 emitted by transducers 21, 22, 23 and 24 (as modulated by pulsar/amplifier 70 and signal multiplexer/filter 73). Peak separation measurer 76 then measures the time separating the two event marks comprising each pair. This parameter represents the time interval occurring between the receipt by a transducer of the first and second echos. A normal echo interval would be obtained from the first echo reflecting off of surface 13 and the second echo being created from ultrasonic wave 72 passing through the entire thickness of part 15 and reflecting off of the back surface. A shorter echo interval results when the second echo travels a shorter than normal path, and is indicative of the second echo being reflected off of a foreign object or flaw in the laminated composite, with the precise length of the abnormally short interval being indicative of the depth of the anomaly beneath surface 13. The echo interval generated by peak separation measurer 76 is digital in form, and its is fed into microcomputer 71.

Lateral position monitor 54 continuously monitors the lateral position of each of transducers 21, 22, 23 and 24, while longitudinal position monitor 60 keeps track of their longitudinal position. The analog outputs of the two position monitors are fed into position integrator 77, which uses them to obtain the location of transducers 21, 22, 23 and 24 on surface 13 in real time. The transducer location coordinates, in digital form, are sent to microcomputer 71. Microcomputer 71 processes the echo interval signals from peak separation measurer 76, and collates them with the corresponding position coordinates of the transducer when it emitted the ultrasonic wave 72 which caused the echos. The collated echo interval signals and position coordinates form echo interval data points, and are stored in mass storage 78.

Preferred embodiment 11 is intended to be rolled longitudinally across surface 13 along a straight line. However, the scope of the invention includes attaching a second longitudinal position monitor to wheel 59 and modifying the programming of position integrator 77 to calculate the overall position coordinates of ultrasonic transducers 21, 22, 23 and 24 when casing 17 is rolled along a curved line as well. Such modifications are within the purview of one skilled in the art.

Plotter 79 is connected to microcomputer 71, and can plot the echo interval data points on paper. Also connected to microcomputer 71 is graphics memory 80, and connected to graphics memory 80 is video monitor 81. The latter two components can visually present the echo interval data points stored in mass storage 78 on the screen of video monitor 81. Independent of whether the echo interval data points are displayed on paper or on screen of videomonitor 81, microcomputer 71 assigns a pixel to each data point, and assigns a shade of gray (or a particular color) to each pixel as a function of the length of the echo interval. Embodiment 11 thus provides for the graphic display of the spatial relationship between the echo interval signals in conjunction with a graphic representation of the subsurface condition indicated by each signal.

Changes and modifications in the specifically described embodiment can be carried out without departing from the scope of the invention, which is intended to be limited only by the scope of the appended claims.

What is claimed is:

1. An apparatus for nondestructively testing the internal composition of objects of differeing shapes and sizes comprising:

a signal producing probe means for producing a probe output of variable value representing a characteristic of the internal composition of a test object;

a casing which houses said probe means;

probe moving means for harmonically moving said probe means relative to said casing and for producing a probe means position output representing the position coordinates of said probe means relative to said casing;

causing positioning means for moving said casing and for producing a casing position output representing the position coordinates of said casing relative to said test object;

integrated position calculator for receiving said casing position output and said probe means position output and for producing an integrated postion output representing the position coordinates of said probe means relative to said test object;

signal collating means for receiving said probe output and said integrated position output, and for pairing said probe output with said integrated position output produced at the time said probe output is produced; and indicating means responsive to said signal collating menas for indicating the correlative relationship between said probe output and said integrated position output that have been paried.

2. The nondestructive testing apparatus defined in claim 1 further comprising:

damping means for damping vibration generated by said probe moving means.

3. The nondestructive testing apparatus defined in claim 2 further comprising:

at least one sensing signal emitted by said probe means;

echoes created by said at least one sensing signal reflecting off of said test object; and said probe output being responsive to said echoes.

4. The nondestructive testing apparatus defined in claim 3 further comprising:

digitalization means for quantizing the level of said probe output into at least two different, discrete levels.

5. The nondestructive testing apparatus defined in claim 4 further comprising;

a coupling gel located on said test object for facilitating the conduction of said at least one sensing signal and said echoes between said probe means and said test object.

6. The nondestructive testing apparatus defined in claim 1 wherein:

said signal collating means includes memory means for storing said probe output and said integrated position output that have been paired; and said indicating means includes means for retrieving from said memory means of said signal collating means said probe output and said integrated position output that have been paired.

7. The nondestructive testing apparatus defined in claim 1 wherein:
said integrated position output is a plurality of integrated position signals;
said probe output is a plurality of probe output signals; and
said indicating means is comprised of video display means for displaying a video scan representation of the spatial relationship between said probe output signals.

8. The nondestructive testing apparatus defined in claim 7 wherein:
said signal collating means includes memory means for storing said probe output signals and said integrated position signals that have been paired in a predetermined memory-mapped format in which said probe output signals and said integrated position signals that have been paired are retrievable in a sequence corresponding to the presentation of said probe output sigaals and said integrated position signals that have been paired on said video display means.

9. The nondestructive testing apparatus defined in claim 8 wherein:
said video display means is comprised of a video monitor and associated control means for generating a visual representation of variations in the level of said probe output signals as a function of the position of said probe means; and
the screen of said video monitor represents a two dimensional field corresponding to an area on said test object which includes points over which said probe means has moved.

10. The nondestructive testing apparatus defined in claim 9 further comprising:
damping means for damping vibration generated by said probe moving means.

11. The nondestructive testing apparatus defined in claim 10 further comprising:
digitalization means for quantizing the level of each of said probe output signals into at least two different, discrete levels.

12. The nondestructive testing apparatus defined in claim 11 wherein:
said casing is sized, shaped and weighted for being manually guided over a surface of said test object.

13. A method for nondestructively testing the internal composition of objects having differing shapes and sizes comprising the steps of:
harmonically moving a sensing probe relative to a casing which houses said sensing probe and moving said casing relative to a test object, to produce a variable level signal representing a characteristic of the internal composition of said test object;
determining the position coordinates of said sensing probe relative to said test object at the moment said test signal is produced;
pairing said test signal with said position coordinates of said sensing probe determined at the moment said test signal is produced; and
displaying said test signal and said position coordinates of said sensing probe that have been paired.

14. The integrated nondestructive testing method defined in claim 13 further comprising the step of:
damping vibration caused by harmonically moving said sensing probe relative to said casing.

15. An apparatus for nondestructively testing the subsurface structure of parts of differing shapes and sizes comprising:
a moveable sensing means for producing a variable sensing means output indicative of the subsurface condition of a test part;
a casing which houses said sensing means;
sensor moving means for harmonically moving said sensing means relative to said casing and for producing a sensing means position output representing the position of said sensing means relative to said casing;
casing moving means for moving said casing relative to said test part and for producing a casing position output representing the position of said casing relative to said test part;
position integration means for integrating said sensing means position output and said casing position output to produce an integrated position output representing the position of said sensing means relative to said test part;
signal collating means for forming at least one data point, with each of said at least one data point being comprised of said sensing means output and said integrated position output produced at the time said sensing means output is produced; and
display means responsive to said signal collating means for graphically representing said at least one data point; whereby
each of said at least one data point pairs a location on said test part with information indicative of the subsurface condition of said test part at such location; and
the subsurface condition of said test part is graphically represented as a function of location on said test part.

16. The apparatus for nondestructively testing subsurface structure defined in claim 15 further comprising:
at least one sensing signal emitted by said sensing means;
echoes created by said at least one sensing signal reflecting off of said test part; and
said sensing means output being responsive to said echoes.

17. The apparatus for nondestructively testing subsurface structure defined in claim 16 wherein:
said sensing means is comprised of at least one ultrasonic transducer; and
said at least one sensing signal is comprised of at least one ultrasonic wave; further comprising
spring means for forcing said at least one ultrasonic transducer to remain in abutment with an opposing surface of said test part and for supporting said at least one ultrasonic transducer so that said at least one ultrasonic wave is normally incident to said opposing surface of said test part.

18. The apparatus for nondestructively testing subsurface structure defined in claim 17 wherein:
said casing moving means is comprised of a plurality of wheels rotatably attached to said casing; and
said sensor moving means is comprised of a plurality of rotatably joined linkages that are rotatably attached to said at least one ultrasonic transducer, and a motor which moves said linkages and, ultimately, said at least one ultrasonic transducer.

19. The apparatus for nondestructively testing subsurface structure as defined in claim 18 further comprising:

damping means for damping vibration generated by said sensor moving means.

20. The apparatus for nondestructively testing subsurface structure as defined in claim 19 wherein:
said sensing means output is a plurality of sensing means output signals;
said integrated position output is a plurality of integrated position output signals; whereby
the Nth of said at least one data point is comprised of the Nth of said sensing means output signals together with said integrated position signal representing the position of the one of said at least one ultrasonic transducer which generated said Nth sensing means output signal at the time said Nth sensing means output signal was generated.

21. The apparatus for nondestructively testing subsurface structure as defined in claim 20 wherein:
said at least one ultrasonic transducer is comprised of a plurality of ultrasonic transducers: and
said plurality of ultrasonic transducers are positioned in a linear array.

22. The apparatus for nondestructively testing subsurface structure as defined in claim 21 wherein;
said wheels rotate about parallel axes;
said linear array of said plurality of ultrasonic transducers is in parallel with said axes; and
said sensor moving means harmonically moves said linear array of ultrasonic transducers along a path which is in parallel with said axes; whereby
said casing moves across said opposing surface of said test part in a direction normal to said path of harmonic motion of said linear array of said plurality of ultrasonic transducers.

23. The apparatus for nondestructively testing subsurface structure as defined in claim 22 further comprising:
excitation means for sequentially and periodically exciting said ultrasonic transducers.

24. The apparatus for nondestructively, testing subsurface structure defined in claim 23 wherein:
said casing is sized, shaped and weighted for being manually guided over said opposing surface of said test part.

25. The apparatus for nondestructively testing subsurface structure as defined in claim 24 further comprising:
a coupling gel located on said opposing surface of said test part for facilitating the conduction of said at least one ultrasonic wave and said echoes between said ultrasonic transducers and said test part.

26. an apparatus for nondestructively testing the subsurface structure of an object comprising:
probe means for emitting a sensing signal and producing a probe output of variable value representing a characteristic of the internal composition of a test object;
a casing which houses said probe means;
said sensing signal being moveable relative to said casing, and said casing being moveable relative to said test object;
signal location means for producing a signal location output representing the position of said sensing signal relative to said casing;
casing location means for producing a casing position output representing the position of said casing relative to said test object;
an integrated position calculator for receiving said casing position output and said signal location output and for producing an integrated position output representing the position of said sensing signal relative to said test object; and
signal collating means for receiving said probe output and said integrated position output, for pairing said probe output with said integrated position output for the respective locations on said test object that are tested, and for producing a collated signal output.

* * * * *